US012778714B1

(12) United States Patent
Sganga et al.

(10) Patent No.: US 12,778,714 B1
(45) Date of Patent: Nov. 3, 2026

(54) SYSTEMS AND METHODS FOR MOUNTING AND SECURING A ROBOTIC MEDICAL SYSTEM

(71) Applicant: Remedy Robotics, Inc., San Francisco, CA (US)

(72) Inventors: Jake Anthony Sganga, San Francisco, CA (US); David James Bell, Mill Valley, CA (US); Armando Armijo, Hayward, CA (US)

(73) Assignee: REMEDY ROBOTICS, INC., San Francisco, CA (US)

(*) Notice: Subject to any disclaimer, the term of this patent is extended or adjusted under 35 U.S.C. 154(b) by 77 days.

(21) Appl. No.: 19/049,670

(22) Filed: Feb. 10, 2025

Related U.S. Application Data

(60) Provisional application No. 63/551,183, filed on Feb. 8, 2024.

(51) Int. Cl.

| | |
|---|---|
| ***A61B 34/30*** | (2016.01) |
| ***A61B 90/57*** | (2016.01) |

(52) U.S. Cl.
CPC .............. *A61B 90/57* (2016.02); *A61B 34/30* (2016.02); *A61B 2034/303* (2016.02); *A61B 2090/571* (2016.02)

(58) Field of Classification Search
CPC ... A61B 90/57; A61B 34/30; A61B 2034/303; A61B 2090/571
See application file for complete search history.

(56) References Cited

U.S. PATENT DOCUMENTS

| | | | | |
|---|---|---|---|---|
| 2017/0086929 | A1* | 3/2017 | Moll | A61B 1/273 |
| 2023/0116397 | A1* | 4/2023 | Devengenzo | B25J 18/02 606/130 |

* cited by examiner

*Primary Examiner* — Vi X Nguyen
(74) *Attorney, Agent, or Firm* — Knobbe Martens Olson & Bear LLP

(57) ABSTRACT

System and methods for mounting a medical robotic system. The system can move within at least four degrees of freedom, providing precise positioning of the medical robotic system. The system can be secured in a locked or unlock state using a plurality of electronic brakes, each of which is in contact with at least one degree of freedom. The plurality of electronic brakes can be released simultaneously via a user input.

24 Claims, 3 Drawing Sheets

SYSTEMS AND METHODS FOR MOUNTING AND SECURING A ROBOTIC MEDICAL SYSTEM

PRIORITY APPLICATION(S)

This application claims priority to U.S. Provisional Application No. 63/551,183, filed Feb. 8, 2024, which is incorporated herein by reference. Any and all applications for which a foreign or domestic priority claim is identified in the Application Data Sheet as filed with the present application are hereby incorporated by reference under 37 CFR 1.57.

BACKGROUND

Field

This application relates to systems and methods of mounting and securing a robotic medical system.

Description

Cardiovascular diseases, including strokes, heart attacks, blood clots, pulmonary embolisms, and the like, are the leading cause of death and disability in the United States and around the world. Much of the negative consequences of cardiovascular disease can be prevented with better access to endovascular intervention (EI). For example, strokes are among the most frequent causes of disability, and outcomes following strokes are directly related to the time it takes to undergo EI. The chance of an individual returning to functional independence drops by over 12% for every hour EI is delayed. However, due to a lack of expertise, EI is available in only 2% of hospitals. This problem is exacerbated by the lack of physical access to hospitals with EI capabilities, with the median time to hospitals with EI capabilities being over three hours. Devastatingly, this means that, for example, two-thirds of large vessel occlusion (LVO) stroke victims in the United States lack timely access to EI.

Despite limited access, EI procedures have been used in modern healthcare for several decades. Such procedures include a specialized tool or medical instrument, typically designed as a slender, flexible, and elongated body, that is carefully inserted and maneuvered through a body lumen or cavity. In some instances, the tools or medical instruments are articulable or controllable, for example, using one or more pull wires, to allow an operator to navigate the tool or medical instrument within the body. Such navigation is often accomplished through deflection (for example, bending) of the distal tip of the tool or medical instrument. This design allows for precise navigation and operation within intricate and delicate vasculature, enabling medical practitioners to perform a variety of diagnostic and therapeutic tasks with minimal invasiveness and enhanced precision. The flexibility and thinness of these instruments are crucial for ensuring patient safety and effectiveness in reaching and treating targeted areas within the body's vascular network.

Some tools or medical instruments are configured for manual control, for example, using knobs or levers mounted on a proximally located handle of the tool or medical instrument. In other instances, the tools or medical instruments can be configured for robotic control, for example, control by a robotic medical system. In other cases, an operator can use the robotic medical system (for example, a controller, user interface, and/or the like) to robotically control the tool or medical instrument.

BRIEF DESCRIPTION OF THE DRAWINGS

Features, aspects and advantages of the present application are described with reference to drawings of certain embodiments, which are intended to illustrate, but not to limit, the present disclosure. It is to be understood that the attached drawings are for the purpose of illustrating concepts disclosed in the present application and may not be to scale.

DETAILED DESCRIPTION

Figure 1:
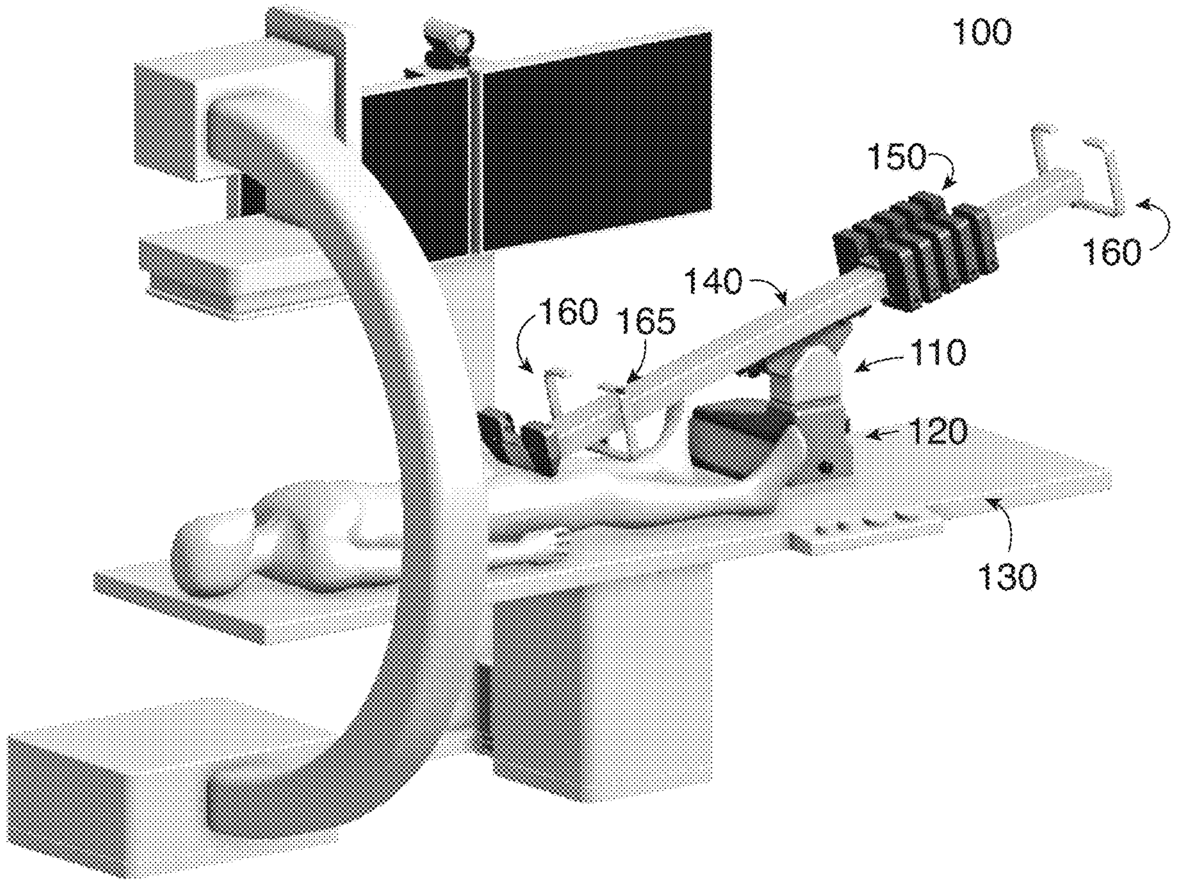
FIG. 1 illustrates an example of system for mounting a medical robotic system.

This application is directed to a mounting and locking system for mounting a medical robotic system, and methods related to the same. In some embodiments, the support system supports the medical robotic system relative to a patient platform and allows the position of at least a portion of the medical robotic system to be adjusted relative to the support system in at least three, four, or five degrees of freedom. In some instances, some or all degrees of freedom can be simultaneously released and/or secured via a user input. For example, the system can include a plurality of electronic brakes associated with the various degrees of freedom that can be instantaneously and simultaneously activated or deactivated. In some instances, the medical robotic system can be manually, electronically, and/or remotely controlled with a user input.

The figures and the following description relate to various example embodiments by way of illustration only. It should be noted that from the following discussion, example embodiments of the structures, methods, systems, and associated models disclosed herein will be readily recognized as viable alternatives that may be employed without departing from the principles of what is claimed. Reference will now be made in detail to several embodiments, examples of which are illustrated in the accompanying figures. It is noted that wherever practicable, similar or like reference numbers may be used in the figures and may indicate similar or like functionality. The figures depict embodiments of the disclosed methods or systems (with select equipment for purposes of illustration) and one skilled in the art will readily appreciate from the following description that various example embodiments of the structures, systems, methods and equipment described herein may be employed without departing from the principles described herein.

This application describes systems and methods for mounting a medical robotic system. In some embodiments, a medical robotic system can be moved or adjusted with respect to three, four, five, or more degrees of freedom, enabling enhanced flexibility and greater accuracy of movement during medical procedures. For example, increased degrees of freedom of movement significantly improves an operator's ability to easily and accurately position the robotic surgical system for complex or risky operations.

The principles described herein can be applicable to robotic medical procedures, for example, where a medical instrument is robotically controlled by a robotic medical system that is configured to insert, retract, roll, and/or articulate instruments based on inputs received from a physician or in a manual, autonomous, or semi-autonomous manner. In some embodiments, the principles of this disclosure may also be applicable to manually controlled medical robotic systems.

The principles of this disclosure are described below with primary reference to examples wherein the medical robotic system is an endovascular medical robotic system, such as an endovascular medical robotic system configured to navigate within the vasculature of the patient. These examples, however, should not be construed as limiting of the principles of the disclosure. Those of skill in the art, upon consideration of the principles disclosed herein, will appreciate that the devices, systems, and methods of mounting and moving the position and/or orientation described herein have application in other contexts. For examples, the principles described herein can be useful with other endoluminal, endoscopic, or laparoscopic tools, instruments, procedures and/or the like. For ease of illustration, however, a primary example related to an endovascular catheter is provided. Accordingly, it should be realized that any of the following description of an endovascular catheter or catheter may also be applied to other endoluminal, endoscopic, and/or laparoscopic tools or the like. Additionally, it should be realized that while this application provides several example configurations for a medical robotic system, including tools or medical instruments, and includes means and method for adjusting configurations of the medical robotic system.

Safe navigation of a catheter within a patient's body generally requires an accurate understanding of the current pose of the catheter. It can be difficult to gain an accurate understanding of pose from a single two-dimensional medical image. For example, a person would have difficulty understanding the exact pose of the catheter from a two-dimensional X-ray image alone. It is difficult to discern whether the catheter lies completely within the plane of the image or is inclined into or out of the plane of the image. Even a highly skilled physicians must rely, in part, on educated guesses based on their understanding of human anatomy. However, uncertainty exists, which increases the risk of damage to the patient during a medical procedure.

Perhaps even more critically, it is extremely difficult, if not impossible, for even skilled physicians to determine the current roll angle of the catheter (i.e., the rotational angle of the catheter about its longitudinal axis). Understanding the current roll of the catheter can be critical for safe navigation, especially considering how most articulable catheters are controlled. Most articulable catheters include pullwires that can be actuated (e.g., tensioned or pulled) to cause deflection of a distal tip of the catheter. Commonly, catheters include four pullwires, each configured to cause deflection of the catheter in one of four cardinal directions. For example, one pullwire can be associated with deflecting the tip of the catheter up, one pullwire can be associated with deflecting the tip down, one pullwire can be associated with deflecting the tip right, and one pullwire can be associated with deflecting the tip down. However, in order to know which pullwire to actuate to cause a given deflection requires an understanding of the current roll position of the catheter. For example, if the distal tip of the catheter is rolled by 90 degrees, actuating the pullwire generally associated with an upward deflection of the tip would instead cause the catheter to articulate (possibly unexpectedly) to the right or left. Unintended articulation can frustrate navigation and cause injury to a patient. Moreover, the distal tip of a catheter often rolls (in unexpected ways) as the catheter is navigated through complex anatomy, such as through a vascular network of a patient, even if roll inputs are not provided at the proximal (e.g., external) end of the catheter.

As will be described in more detail below, the systems, methods, and devices provide for accurate movement and positioning of a medical robotic system, including, for example, embodiments for which the medical robotic system comprises an endovascular catheter. The methods and systems described herein can also be used with biplane imaging systems to determine degrees of freedom of movement estimates of the medical robotic system. In some embodiments, determination of, e.g., horizontal, vertical, pitching, yawing, and similar motions can be determined from medical images, including X-ray biplane images and/or three-dimensional scan images.

In some aspects, this application describes a system to mount a medical robotic system to or relative to a patient platform. In some embodiments, the medical robotic system includes a support system that provides at least three, four, or five degrees of freedom for positioning, adjusting and/or moving the medical robotic system. In some embodiments, the medical robotic system utilizes a plurality of electronic brakes associated with each degree of freedom to securely lock the position of the medical robotic system.

In some further aspects, this application describes a method of positioning a medical robotic system in relation to a patient platform. In some embodiments, the method comprises using a support system to hold the medical robotic system and adjusting the position of the support system about at least three, four, or five degrees of freedom. In some embodiments, the movement of the medical robotic system is controlled by electronic brakes coupled with the at degrees of freedom.

FIG. 1 illustrates an example of system for mounting a medical robotic system 100. As shown, FIG. 1 illustrates an example embodiment of a medical robotic system 100 that can be mounted, for example, on a patient platform 130. In some alternative embodiments, the medical robotic system can be mounted on a platform, a bed, a horizontal surface, and the like. In some embodiments, the medical robotic system comprises a support system 110. For example, the support system can be configured to support the medical robotic system. In some further embodiments, the support system 110 is coupled with a linear translation mechanism 120.

In some embodiments, the support system 110 can be configured to provide motion and adjustment of the medical robotic system 100 in three, four, or more degrees of freedom with respect to the support system 110. For example, a first degree of freedom can enable the medical robotic system 100 to move horizontally with respect to the support system 110; a second degree of freedom can enable the medical robotic system 100 to pitch with respect to the support system 110; a third degree of freedom can enable the robotic system 100 to yaw with respect to the support system 110; and a fourth degree of freedom can enable the robotic system 100 to move vertically with respect to the support system 110. In some embodiments, each of the degrees of freedom move with respect to at least one joint, for example, a rotational joint, a translational joint, a ball-and-socket joint, a twisting joint, a colinear joint, a revolving joint, and similar joints as understood by one having skill in the relevant art.

In some embodiments, the medical robotic system 100 can comprise a linear translation mechanism 120. For example, the linear translation mechanism 120 can provide an additional degree of freedom with respect to the patient platform 130. In some embodiments, the linear translation mechanism 120 can move along the length of the patient platform 130. In some embodiments, the linear translation mechanism 120 can move along the width of the patient platform 130. In some embodiments the linear translation mechanism 120 can move along both the length and the width of the patient platform 130.

In some embodiments, the medical robotic system 100 can comprise a beam 140. In some embodiments, the beam 140 is coupled with the support system 110. In some further embodiments, the beam 140 can be coupled with at least one ballast 150 or counterweight. For example, the at least one ballast 150 can stabilize and counterbalance the beam 140 with respect to a zone of coupling of the beam with the support system 110. In some embodiments, the beam 140 is coupled with a lifting loop 160. For example, the lifting loop 160 can be used to guide the motion and positioning of the medical robotic system 100 with respect to the patient platform 130, the support system 110, and/or the linear translation mechanism 120.

Figure 2:
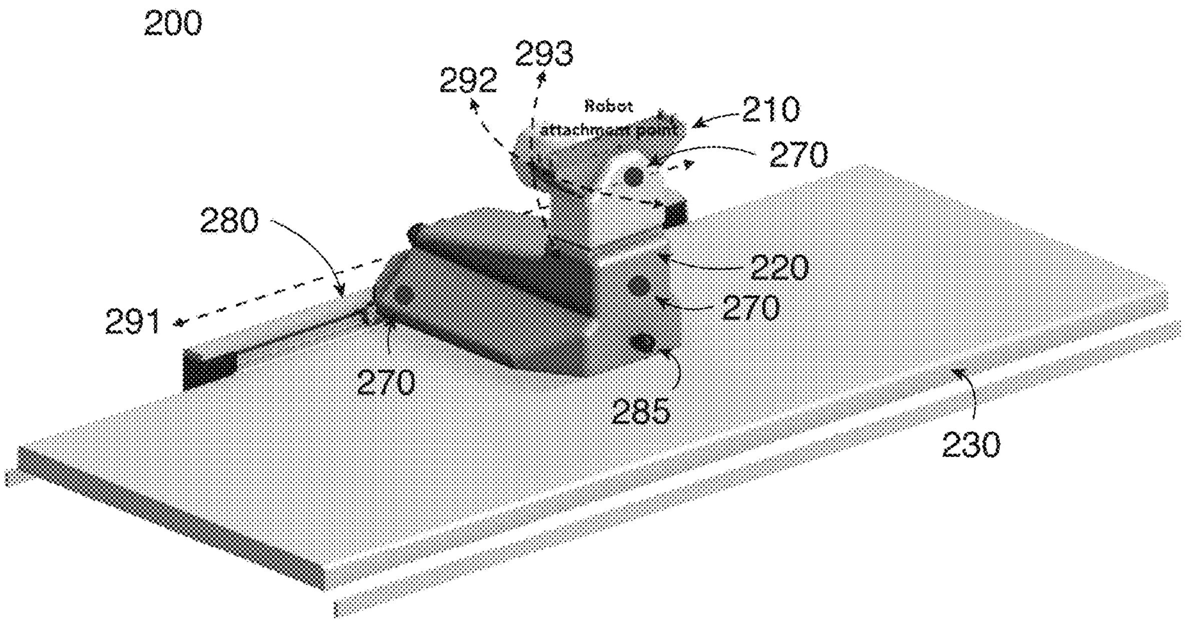
FIG. 2 illustrates an example support system and linear translation mechanism for mounting a medical robotic system.

FIG. 2 illustrates an example support system 210 and linear translation mechanism 220 for mounting a medical robotic system 200. For example, in some embodiments, the medical robotic system 200, can comprise three, four, or more degrees of freedom. As illustrated in FIG. 2, a first of freedom 291 can comprise horizontal motion, e.g., allowing the medical robotic system 200 to change its horizontal orientation with respect to the patient platform 230. In some embodiments, a second degree of freedom 293 can comprise a pitching motion, e.g., allowing the medical robotic system to 200 to change its angular orientation with respect to the support system 210 along a vertical plane. In some embodiments, a third degree of freedom 292 can comprise a yawing motion, e.g., allowing the medical robotic system to 200 to change its angular orientation with respect to the support system 210 along a horizontal plane. In some embodiments, a fourth degree of freedom can comprise vertical motion, e.g., moving up and down, of the medical robotic system 200 with respect to the patient platform 230. In some embodiments, further degrees of freedom can comprise rotary motion, reciprocating motion, oscillating motion, helical motion, gear train motion, rack and pinion motion, belt and pulley motion, chain and sprocket motion, screw motion, and/or planetary motion. It should be understood that reference herein to a "first," "second," and "third" degree of freedom is solely for illustrative purposes. For example, in some embodiments, a first degree of freedom can comprise yawing, whereas in an alternative embodiment, a first degree of freedom can comprise pitching, etc.

In some embodiments, motion of the linear translation mechanism 220 can be guided by one or more rails 280. For example, the linear translation mechanism 220 can be coupled with a sliding carriage that engages with one or more rails 280 to provide linear motion of the medical robotic system 200 with respect to the length of the patient platform 230. In some further embodiments, the linear translation mechanism 220 can be coupled with a sliding carriage that engages with one or more rails 280 to provide linear motion of the medical robotic system 200 with respect to the width of the patient platform 230.

In some embodiments, the movement or adjustment of the medical robotic system 200 can be secured with a plurality of electronic brakes 270. For example, one or more electronic brakes, such as one or more electromagnetic brakes, can be coupled to each degree of freedom of motion of the medical robotic system 200. In some embodiments, the plurality of electronic brakes can be coupled to the linear translation mechanism 220. In some embodiments, the plurality of electronic brakes 270 can be coupled with a user input. For example, a user input can comprise a button, switch, lever, solenoid, a joystick, a touchpad, and like mechanisms as would be understood by one skilled in the relevant art. In some embodiments, the user input can contact and/or control each of the plurality of electronic brakes 270 simultaneously. In some embodiments, the plurality of electronic brakes 270 can be configured such that the default state of the brakes is the locked position. The user can actuate the user input to release the electronic brakes 270 to allow for adjustment of the position of the robotic medical system. In some instances, actuating the user input releases all of the brakes 270 simultaneously. With the robotic system positioned as desired, the user may release the user input to resecure the brakes, holding the position of the robotic system in place.

In some examples, for example, as shown in FIG. 1, the user input 165 can be provided a lifting loop 160 or handle associated with the robotic system 100. This position for the user input 165 can be advantageous as the user can release the electronic brakes (by actuating the user input 165) while simultaneously gripping the handle to reposition the robotic system.

In some embodiments, the mounting system 200 can include emergency stop input 285. For example, actuating the emergency stop input 285 preventing all movement of the medical robotic system 200 (e.g., insertion of a robotically controlled catheter).

In some embodiments, the medical robotic system is configured to provide access to a femoral artery and/or a radial artery of a patient.

In some embodiments, the medical robotic system can comprise a lateral platform detachably coupled with the patient platform. For example, the lateral platform can be configured to provide increased width to at least a portion of the patient platform.

Figure 3:
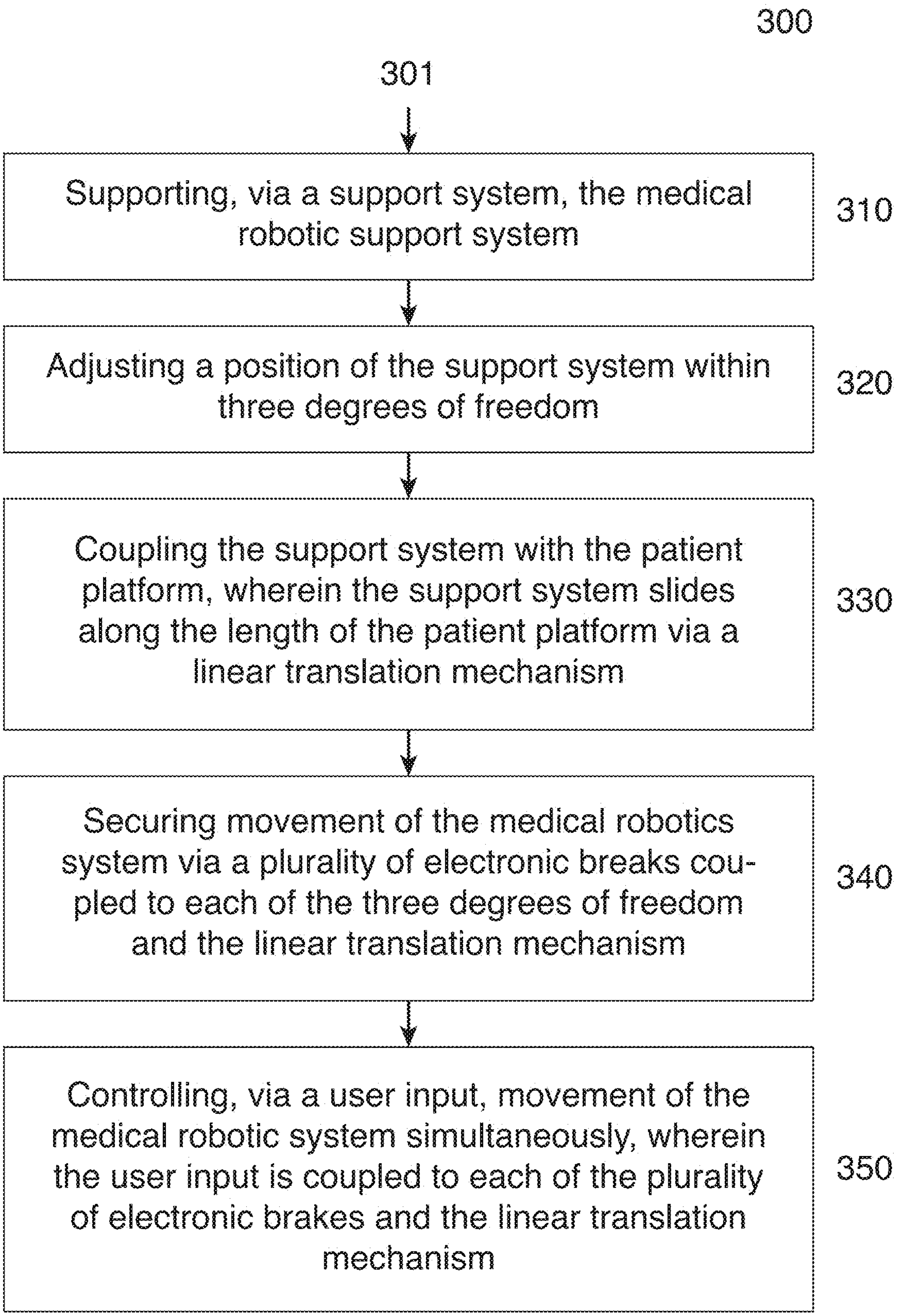
FIG. 3 illustrates an example method of mounting a medical robotic system.

FIG. 3 illustrates an example method of mounting a medical robotic system 300. In some embodiments, a method of mounting a medical robotic system relative to a patient platform 301. In some embodiments, the method 300 comprises supporting, via a support system, the medical robotic system 310. In some embodiments, the method 300 comprises adjusting the position of the support system within four degrees of freedom 320. In some embodiments, the method 300 comprises coupling the support system with the patient platform wherein the support system slides along the length and/or width of the patient platform via a linear translation mechanism 330. In some embodiments, the method 300 comprises securing movement of the medical robotic system via a plurality of electronic brakes coupled to each of the four degrees of freedom and the linear translation mechanism 340. In some embodiments, the method 300 comprises controlling, via a user input, movement of the medical robotic system simultaneously, wherein the user input is coupled to each of the plurality of electronic brakes and the linear translation mechanism.

In some instances, the term "pose" is used herein to refer to the position and orientation of a catheter. In some embodiments, determination of pose can be made based on a two-dimensional image, for example, a medical image such as a single plane X-ray image, and/or one or more radio-opaque markers included on a catheter. Computer vision models can be employed to detect the radio-opaque markers in the two-dimensional medical image and to determine the pose of the catheter therefrom.

As used herein, "degrees of freedom" refers to the number of independent parameters or directions in which a mechanical system or physical body can move or rotate. In some embodiments, the pose can be defined by one or more degrees of freedom. In some instances, the pose can be defined by five degrees of freedom for the catheter. The five degrees of freedom can include two positional degrees of freedom (e.g., x and y position) and three degrees of freedom relating to orientation (e.g., heading, incline, and roll). In other embodiments, the pose can comprise greater (e.g., six) or fewer (e.g., four or fewer) degrees of freedom. While this application primarily describes examples of pose in terms of x, y, and z for position, and heading, incline, and roll for orientation, other methods for describing or defining the pose (e.g., alternative coordinate systems, alternative naming conventions, etc.) are possible, and the principles of this application extend to all methods for defining pose. Further, in some embodiments, the methods and systems of this application may be used to determine one, more than one, or all elements of pose.

As used herein, "position" refers to the three-dimensional coordinates of an object or system in a defined reference frame, encompassing both its location and orientation relative to a known point or axis. In some embodiments, position can refer to, for example, an x, y, and z position (for example, a location within three-dimensional space). In some embodiments, position can refer to the x and y position within the two-dimensional image plane of a medical image, such as an X-ray. Orientation can be represented in many different ways. In general, in this application, orientation is referred to using three Euler angles: (1) heading, which can be a measure of angulation or articulation about the z-axis and/or where the device is pointing in the image plane; (2) incline, which can be a measure of rotation about the x-axis and/or where the device is pointing out of the image plane (e.g., pitch); and (3) roll which can be a measure of rotation about the longitudinal or central axis of the catheter.

As used herein, "secure," "securing" and similar variations as would be understood by one having skill in the relevant art, refer to a state or process where access to a physical, electronic or digital entity is selectively restricted or permitted through the implementation of control mechanisms or protocols. In some embodiments, securing can comprise locking (e.g., preventing movement, access, use, etc.), and/or unlocking (e.g., permitting movement, access, use etc.). In some embodiments, a secured state is achieved through the application of hardware, software, or a combination thereof, which enforces rules or conditions that must be met for the transition between locked (restricted access) and unlocked (granted access) states. In some embodiments, securing comprises actuation via a user input, such as a button, switch, lever, solenoid, a joystick, a touchpad, and like mechanisms as would be understood by one skilled in the art.

It will now be evident to those skilled in the art that there has been described herein methods, systems, and devices for improved mounting of a robotic medical device. Although the inventions hereof have been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary, it is intended to cover any and all equivalents that may be employed without departing from the spirit and scope of the inventions.

While the disclosure has been described with reference to certain embodiments, it will be understood that various changes may be made, and equivalents may be substituted for elements thereof without departing from the scope of the disclosure. In addition, many modifications will be appreciated to adapt a particular instrument, situation, or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter or microcatheter" or "advancing one portion of the device (e.g., linearly) relative to another portion of the device to rotate the distal end of the device" include instructing advancing a catheter" or "instructing advancing one portion of the device," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A system for mounting a medical robotic system relative to a patient platform, the system comprising:

a support system configured to support the medical robotic system, the support system further configured to provide at least four degrees of freedom for adjusting a position of the medical robotic system;

a linear translation mechanism configured to provide at least one of the at least four degrees of freedom and configured couple the support system to the patient platform, the linear translation mechanism slidingly engaged with the support system such that the support system is moveable along a length and/or a width of the linear translation mechanism;

a plurality of electronic brakes, wherein each of the at least four degrees of freedom are coupled with at least one of the plurality of electronic brakes, and wherein the plurality of electronic brakes secure movement of the medical robotic system; and a user input coupled with the plurality of electronic brakes, wherein the user input is configured to release each of the plurality of electromagnetic brakes simultaneously.

2. The system of claim 1, wherein securing comprises a locked or unlocked state.

3. The system of claim 1, wherein the at least four degrees of freedom comprise at least:

a first degree of freedom for providing horizontal motion of the medical robotic system relative to the support system;

a second degree of freedom for providing pitching motion of the medical support system relative to the support system;

a third degree of freedom for providing yawing motion of the medical support system relative to the support system; and a fourth degree of freedom for providing vertical motion of the medical support system relative to the support system.

4. The system of claim 1, wherein the linear translation mechanism is configured to move with respect to a length and/or a width of the patient platform.

5. The system of claim 1, wherein each of the four degrees of freedom move with respect to at least one rotational joint.

6. The system of claim 1, wherein the linear translation mechanism is coupled with at least one sliding carriage, the linear translation mechanism mounted on at least one rail, wherein the rail is coupled with at least an operating side of the patient platform, a non-operating side of the patient platform, or both.

7. The system of claim 1, further comprising a beam coupled with the support system.

8. The system of claim 7, wherein the beam is coupled with one or more ballasts configured to stabilize and counterbalance the beam.

9. The system of claim 7, wherein the beam is coupled with at least one lifting loop, wherein the at least one lifting loop is configured adjust the position of the medical robotic system about any one of the three degrees of freedom and the linear translation mechanism relative to the support system.

10. The system of claim 1, wherein each of the plurality of electronic brakes are configured to default to a locked state.

11. The system of claim 1, wherein the system for mounting is configured to position the medical robotic system to provide access to a femoral vessel and/or a radial vessel of a patient.

12. The system of claim 1, further comprising a lateral platform detachably coupled with the patient platform, wherein the lateral platform is configured to provide increased width to at least a portion of the patient platform.

13. A method of mounting a medical robotic system relative to a patient platform, the method comprising:

supporting, via a support system, the medical robotic system;

adjusting a position of the support system within four degrees of freedom;

coupling the support system with the patient platform, wherein, via a linear translation mechanism, the support system slides along the length of the patient platform;

securing movement of the medical robotic system via a plurality of electronic brakes coupled to each of the four degrees of freedom and the linear translation mechanism; and controlling, via a user input, movement of the medical robotic system simultaneously, wherein the user input is coupled to each of the plurality of electronic brakes and the linear translation mechanism.

14. The method of claim 13, wherein securing comprises locking or unlocking.

15. The method of claim 13, wherein adjusting comprises:

moving horizontally the medical robotic system relative to the support system within a first degree of freedom;

pitching the medical robotic system relative to the support system withing a second degree of freedom;

yawing the medical robotic system relative to the support system within a third degree of freedom; and moving vertically the medical robotic system relative to the support system with a fourth degree of freedom.

16. The method of claim 13, wherein the linear translation mechanism moves with respect to a length and/or width of the patient platform.

17. The method of claim 13, further comprising, via a rotational joint, movement of each of the four degrees of freedom.

18. The method of claim 13, wherein the linear translation mechanism, via a sliding carriage, slides about at least one rail, the at least one rail coupled with at least an operating side of the patient platform, a non-operating side of the patient platform, or both.

19. The method of claim 13, further comprising a beam coupled with the support system.

20. The method of claim 19, wherein the beam is coupled with one or more ballasts, the one or more ballasts stabilizing and counterbalancing the beam.

21. The method of claim 19, wherein the beam is coupled with at least one lifting loop, the at least one lifting loop guiding movement of the medical robotic system about any one of the four degrees of freedom and the linear translation mechanism relative to the support system.

22. The method of claim 13, wherein each of the plurality of electronic brakes are locked by default.

23. The method of claim 13, wherein the system for mounting is configured to position the medical robotic system to a femoral vessel and/or a radial vessel of a patient.

24. The method of claim 13, further comprising detachably coupling a lateral platform with the patient platform, wherein the lateral platform is configured to provide increased width to at least a portion of the patient platform.

* * * * *